United States Patent [19]

Smith

[11] 4,250,577
[45] Feb. 17, 1981

[54] FACE MASK FOR USE WITH GOGGLES

[76] Inventor: Robert P. Smith, P.O. Box 700, Evergreen, Colo. 80439

[21] Appl. No.: 59,227

[22] Filed: Jul. 20, 1979

[51] Int. Cl.³ .............................................. A61F 9/02
[52] U.S. Cl. .............................................. 2/427; 2/9
[58] Field of Search ................ 2/427, 9, 10, 205, 206

[56] References Cited

U.S. PATENT DOCUMENTS

| | | | |
|---|---|---|---|
| 3,298,031 | 1/1967 | Morgan | 2/9 |
| 3,678,929 | 7/1972 | Buscher | 2/427 X |
| 4,095,290 | 6/1978 | O'Brien | 2/9 |

FOREIGN PATENT DOCUMENTS 390685  8/1908  France .............................................. 2/9

Primary Examiner—Peter P. Nerbun
Attorney, Agent, or Firm—Richard D. Law

[57] ABSTRACT

A face mask shaped for the lower face below eye covering goggles includes a central attachment for securing to the nose piece of the goggles, and side holders for securing to the sides of the goggles, and a verturi nose covering on the mask to draw exhaled air from behind the mask permitting a fresh air flow behind the mask while moving.

4 Claims, 9 Drawing Figures

FACE MASK FOR USE WITH GOGGLES

BACKGROUND OF THE INVENTION

This invention relates to lower face coverings of a generally imperforate form to prevent face injury from flying rocks and the like, including means for providing a continuous flow of fresh air for the user.

The racing of motorcycles, or merely riding in groups, involves dangers other than accidents. Most usually the rider is unprotected particularly around the face areas. Flying insects and debris, such as rocks and gravel kicked up from other machines, may be very damaging to a rider when struck in the face. Goggles are an essential item for eye protection, but with only goggles the remainder of the face is unprotected. Transparent full face shields are used in some instances, but physical exertion causes heavy breathing, with the fogging of the transparent lens being an unsavory by product.

Winter sports such as skiing, snowmobiling and the like, involves passage of the sports fan in air. If the air is cold, the danger of frostbite is real. Usually frostbite occurs rapidly and unexpectedly. Experienced winter sports addicts protect their faces from frostbite by face masks, etc. below goggles, but the usual type tends to cause fogging of goggle lenses.

THE PRESENT INVENTION

According to the present invention, there is provided a lower face shield arranged for use with goggles, and provided with means for ventilating the space between the mask and face, with a continuous flow of fresh air during movement. The unit is arranged with a venturi nose piece which pulls air from the space behind the mask when the mask is moved through the air. Formed of an imperforate synthetic plastic, which is rigid enough to maintain its shape, and is resilient and flexible enough to be bent, the mask is easily attached to or disengaged from a goggle, and provide a protective covering for the lower face. The plastic mask is capable of withstanding rather sever impacts in stopping objects from hitting the face.

OBJECTS AND ADVANTAGES OF THE INVENTION

Included among the objects and advantages of the present invention is to provide a mask arranged to be secured on and supported by a goggle.

Another object of the invention is to provide a face mask for protecting a user's face below a goggle.

Still another object of the invention is to provide a generally imperforate face mask arranged with a venturi ventilator to maintain a continuous flow of air in the space between the user's face and the mask.

Yet another object of the invention is to provide an easily mounted and removed face mask on goggles.

A further object of the invention is to provide a lower face mask for use in the protection of the user from flying rocks, gravel and the like.

These and other objects and advantages of the invention may be readily ascertained by reference to the following description and appended illustrations.

GENERAL DESCRIPTION OF THE DRAWINGS

SPECIFIC DESCRIPTION OF THE DRAWINGS

Figure 1:
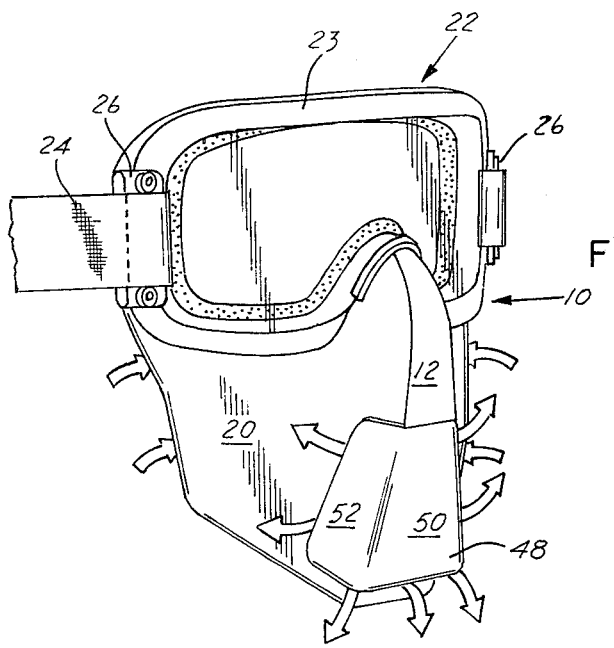
FIG. 1 is a perspective view of a face mask according to the invention, mounted on a full lens goggle.
Figure 3:
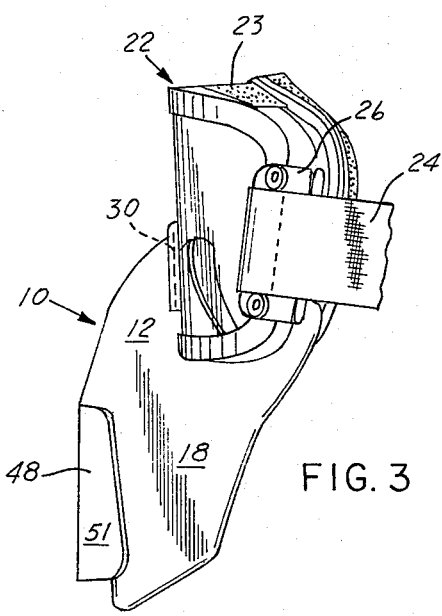
FIG. 3 is a side elevational view of the mask of FIG. 2.
Figure 2:
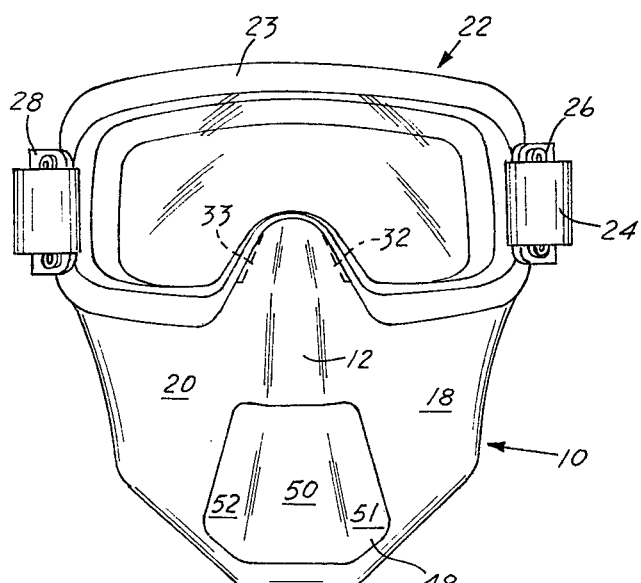
FIG. 2 is front elevational view of a face mask according to the invention.
Figure 4:
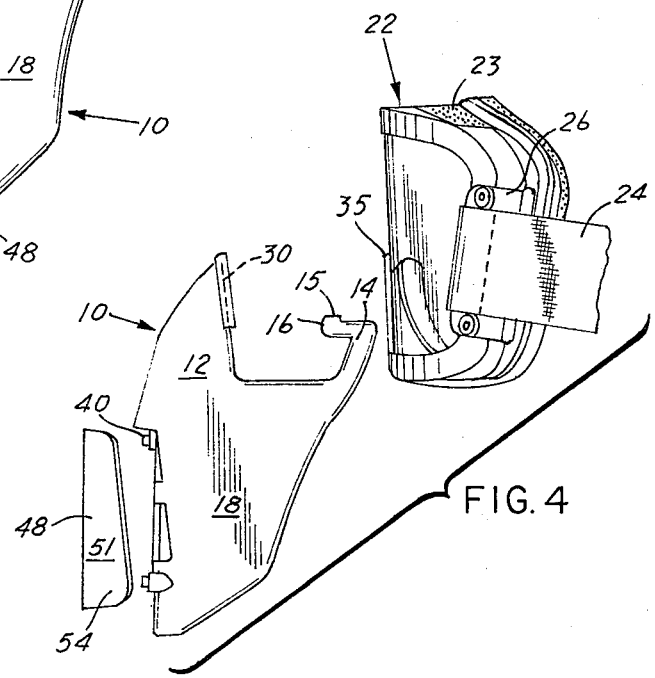
FIG. 4 is an exploded side view of a face mask and a goggle in position for assembly of the mask on the goggle.
Figure 5:
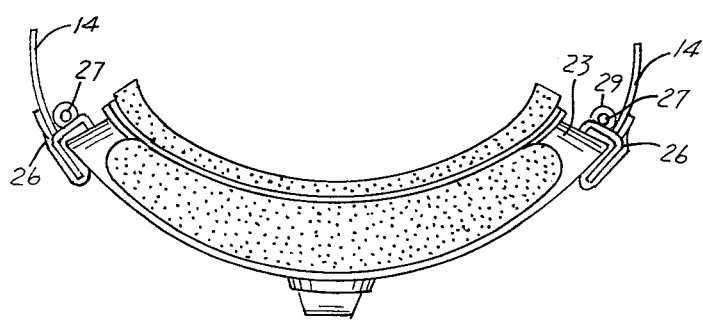
FIG. 5 is a top view of the assembly of FIG. 2.
Figure 6:
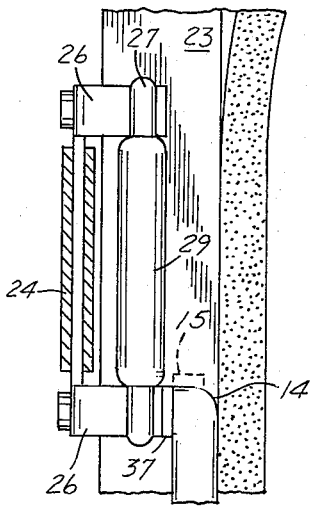
FIG. 6 is a side elevational detail of a side hook on a mask in holding position on a goggle.

In the device selected for illustration is a preferred embodiment, and in FIGS. 1-9, a lower face mask, shown generally as numeral 10, includes a nose section 12 and upper attaching hooks 14 and 16 on sides. The nose section accommodates the nose of a user without touching the nose. Extending rearwardly on right side of the nose section is cheek section 18 and on the left side is cheek section 20. These sections are sized and shaped to extend around to about the side ends of the goggle, shown generally by numeral 22. This goggle is illustrated with a full lens (or a one piece lens covering both eyes). Also, the goggle may include two close spaced parallel goggle lens (coextensive) to provide a dead air space between them, to prevent fogging. The goggle is conventional held on a user's head by a head strap or band 24 secured to a bail 26 on one side and a bail 28 on the other side. The face mask is preferable made of a synthetic plastic which is capable of withstanding the impact of sizable rocks or pebbles, and thus is preferably resilient and somewhat flexible in the thickness to provide adequate protection. The mask is preferably semi-rigid which is relatively soft, but of sufficient rigidity to maintain its shape in use. One material which is satisfactory is a polyproylene. The mask is made of a size to extend around the face and to hide the face surface below the goggle, which includes covering the chin.

Figure 9:
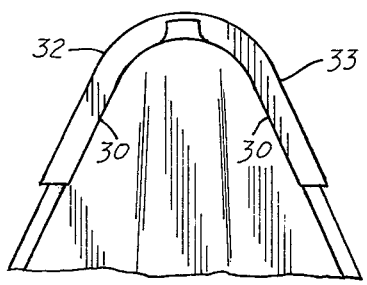
FIG. 9 is an enlarged detail of the nose section of the mask.
Figure 8:
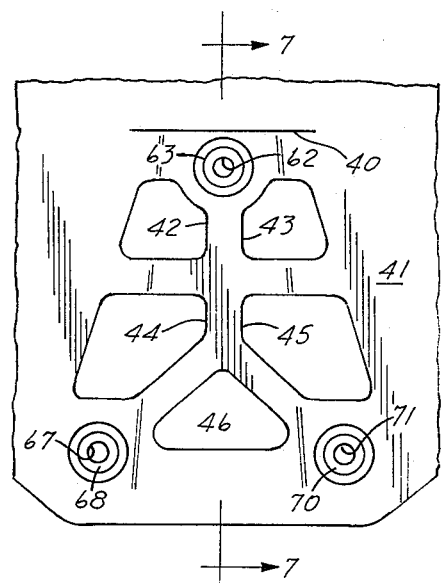
FIG. 8 is front elevational detail of the breathing openings of the face mask of the invention.

The face mask is secured to the nose section of a goggle frame by a friction fit of a groove over the top of the goggle nose section. A groove 30, FIG. 9, is produced by flaps 32 and 33. This groove is generally of the shape of the goggle nose frame and is pressed onto the nose section 35 of the goggle frame 23, securing it by friction. The nose section of the goggle holds the goggle lens, and thus extends above the edge of the lens. The upper side ends of the face mask are secured to the goggle frame by hooks 14 and 16 pressed into an opening 37 (FIG. 6) in the goggle frame 23 adjacent the bail 26. The bail 25 is held by a pin 27 held in a tubular 29 piece of frame 23. Upstanding ends on the hooks, as end 15 on hook 14, aids in holding the hooks in the openings and thereby securing the face mask to the goggle frame.

The face mask extends from a forward position centerwise of the mask rearwardly generally around the user's face. The nose section 12 terminates in relatively sharp undercut 40, and a perforate mask section 41 including breathing openings 42, 43, 44, 45 and 46 extends over the lower nose and mouth of the user. These openings are arranged to be below the user's nose, but in a position to be impinged upon by the user's breath. A nose cover 48, generally including a planar center section 50 and rearwardly angled right wing 51 and rearwardly angled left wing 52 is releasably mounted over the openings 42, 43, 44, 45 and 46, however, leaving a space between the edge of the wings and the face mask, and at the bottom of nose piece 54 and the lower part of the face mask.

Figure 7:
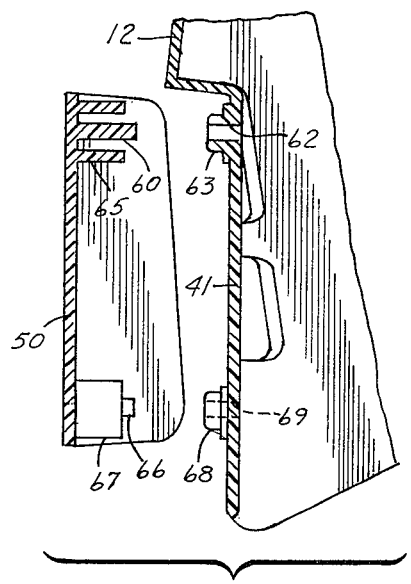
FIG. 7 is a side elevational detail view, in section, of a removable nose piece for fitting on the face mask of the invention.

The nose cover 48 is releasably secured to the face mask by means of pins in corresponding, aligned openings on the face mask. In FIG. 7, a pin 60 is arranged to telescope in opening 62, having an annular reinforcing, integral grommet 63 around the opening facing outwardly. An annular reinforcing grommet 65 for the pin 60 is arranged telescopes over the grommet 63 providing an additional holding member. In a similar manner, pins and grommets telescope over a pair of spaced reinforced openings at the bottom of the nose cover. Thus, pin 66 in grommet 67 mates with opening 69 having a reinforcing grommet 68, which telescopes in the annular space between the pin and the grommet 67. A similar grommet 70 reinforces opening 71 and accommodates another pin on the other side of the bottom of the nose cover. This provides a three point attachment for nose cover. These attaching means, also, support the nose cover away from the imperforate material of the face mask leaving the space around the nose piece.

Supporting the nose cover spaced from the face mask, FIG. 1, leaves an opening around the two sides and bottom of the nose covering. The nose cover 48 is shaped so that the wings flare outwardly and rearwardly and the passage of air over the nose cover produces increased air velocity as the air approaches the rear edges of the nose cover. This causes a reduction in pressure at the opening around the nose cover, in a venturi effect, aspirating air through the openings 42–46 in the face mask. This causes a flow of air around the edges of the face mask, thereby bringing in fresh air into the space in front of the user's face. The flow of air is continuous as long as the mask is moving through the air.

The venturi effect is obtained when the mask is moved forwardly through the air, as when the user is being propelled forwardly. The higher the velocity of the user, the greater is the flow of air. The face mask is highly beneficial for motorcycle riders in racing or in any type of operation. Since a motorcycle may be driven at high rates of speed, the venturi effect maintains a substantial flow of air around the user's face behind the mask.

The face mask is very usable for motorcycle riders to prevent injury from flying objects. It, also, protects the face from wind and cold. For skiers, the face mask provides frosbite protection, which, of course, is similar for snow mobilers. The nose piece arrangement and the spaced fit of the mask away from the user's face prevents a back pressure and a build up of stale air from the user's breathing. In very hot weather the nose cover may be removed to have a direct flow of air into the openings 42–46, while providing protection from flying objects. It is, also, possible to cut off a portion of the bottom of the face mask, when the user has a full helmet, with an opening for the eyes and nose but with a wide chin area. This provides full face protection with the helmet, the goggle and partial face mask.

The face mask, as illustrated, is intended to fit a particular shape of goggle, however, the fastening design may be changed to suit a particular design of goggle.

Since a face mask is desired by a motorcycle rider, skier, snowmobiler, etc. at all times, the easy removability is highly functional. Also, the easy and fast assembly is an asset to the unit. The durability of the face mask normally outlasts the goggle lenses, and is therefore, an economic advantage. The plastic material may be colored or tinted to provide matching or contrasting colors with the user's helmet, clothing or the like.

What is claimed is:

1. A lower face mask for use with a goggle comprising:
   (a) a nose section arranged to cover the nose of a user,
   (b) securing means on said nose section for securing the same to a goggle frame,
   (c) cheek sections integral with and extending laterally and rearwardly of said nose section shaped so as to cover the user's lower face and be spaced from the face of the user and having terminating ends at about the side limits of the goggle,
   (d) attachment means at the terminating ends of said cheek sections for attachment to a goggle frame,
   (e) a perforate section below said nose section,
   (f) venturi action cover means for said perforate section secured to and generally spaced from said perforate section including outwardly and rearwardly extending wing portions spaced from the lower cheek sections of the mask, and
   (g) attachment means for securing said cover means over said perforate section and spaced therefrom so as to maintain a space between at least the side edges of said wing portions and said mask for a venturi action flow of air from the inside of said face mask through said perforate section caused by air passing over said venturi action cover means.

2. A lower face mask according to claim 1, wherein said nose section and said cheek sections are arranged to normally be spaced from the face of the user.

3. A lower face mask according to claim 1, wherein said venturi action cover means is releasably attached to the mask by said attachment means.

4. A lower face mask according to claim 1, wherein said venturi action cover means is generally arcuate and secured to maintain a space between its side edges of the wings and the bottom thereof and said mask.

* * * * *